(12) United States Patent
Linton

(10) Patent No.: US 7,210,812 B1
(45) Date of Patent: May 1, 2007

(54) COMBINATION SCENT-DISTRIBUTER/FLASHLIGHT FOR A HUNTER

(76) Inventor: Ronnie L. Linton, 712 Southfield Dr., Evansville, IN (US) 47715

( * ) Notice: Subject to any disclaimer, the term of this patent is extended or adjusted under 35 U.S.C. 154(b) by 47 days.

(21) Appl. No.: 11/219,361

(22) Filed: Sep. 6, 2005

(51) Int. Cl.
*F21L 4/00* (2006.01)
*F21L 13/00* (2006.01)

(52) U.S. Cl. .................... 362/183; 362/643; 422/124

(58) Field of Classification Search ........... 362/183, 362/157; 422/124
See application file for complete search history.

(56) References Cited

U.S. PATENT DOCUMENTS

| | | | |
|---|---|---|---|
| 4,149,224 A | 4/1979 | King et al. | |
| D275,328 S | 8/1984 | Yin et al. | |
| 4,937,431 A | 6/1990 | Jameson et al. | |
| D351,901 S | 10/1994 | Boruch et al. | |
| 6,033,212 A | 3/2000 | Bonnema et al. | |
| 6,589,487 B1 * | 7/2003 | Ly et al. .................... | 422/125 |
| 6,955,450 B2 * | 10/2005 | Johnson .................... | 362/253 |
| 2002/0012246 A1 * | 1/2002 | Rincover et al. ........... | 362/186 |

* cited by examiner

*Primary Examiner*—Sandra O'Shea
*Assistant Examiner*—James W Cranson, Jr.
(74) *Attorney, Agent, or Firm*—Donald R. Schoonover

(57) ABSTRACT

A scent-distributor/flashlight having a light-producing portion with a battery, an illumination mechanism operably connected to the battery through a switch mechanism, and a first adapting mechanism having a plurality of female connectors. The invention also has a scent-producing portion with a second housing having a cavity, an intake vent, and an output vent; a second adapting mechanism having a plurality of male connectors for mating with the female connectors to physically connect the scent-producing and light-producing portions together as a unit, and to connect the male connectors to the switch mechanism of the light-producing portion. The scent-producing portion also includes a container with a wick for releasing a combination scent-distributor/flashlight scent contained in the container, and a motor-driven fan connected through the male connectors to the switch mechanism and the battery for drawing ambient air through the intake vent, circulating that air across and around the wick, and exhausting that air through the output vent.

9 Claims, 1 Drawing Sheet

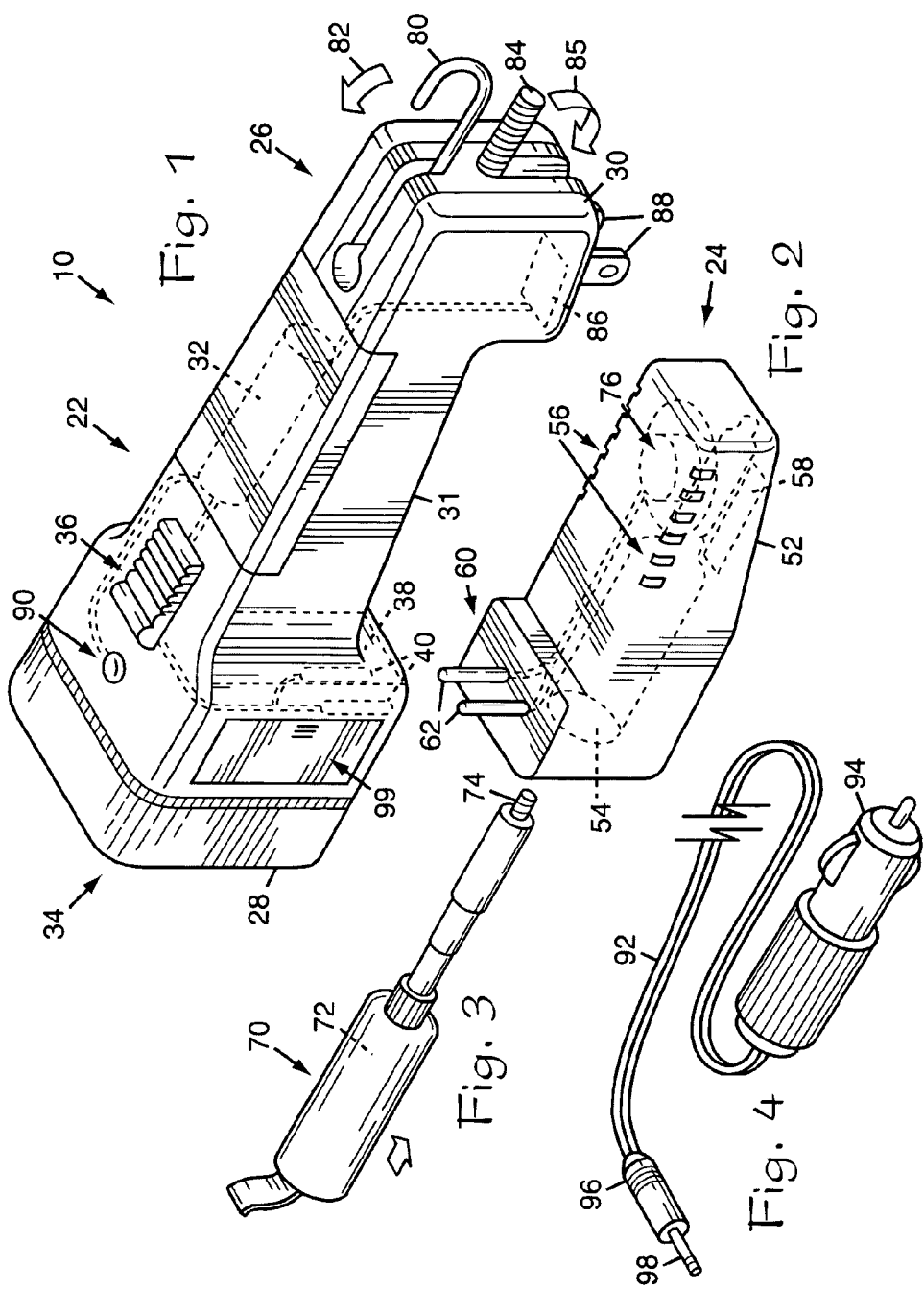

COMBINATION SCENT-DISTRIBUTER/FLASHLIGHT FOR A HUNTER

BACKGROUND OF THE INVENTION

1. Field of the Invention

The present invention relates to sporting goods and, more specifically without limitation, to accessories for hunters.

2. Description of the Related Art

Hunting is a popular activity enjoyed by millions of people worldwide. Although a large segment of the hunter population participates on a recreational level, it is recognized that hunting is also a major food-acquiring and producing industry in some parts of the world. Both large and small game are sought after for sport and for food in most of the land-based ecological systems of the world. Regardless of the reason for hunting, people of all ages enjoy doing so in fields, forests, and plains as the climate and season of the year permit.

A hunter is one of the most diversely equipped of all outdoor sportsmen. The basic item needed to hunt is a weapon with lethal capability. Bait or some type of attraction device is sometimes useful in drawing a prey into range. So, one might find a hunter with a rifle, shotgun, or bow and arrow along with a scented lure or a calling device of some sort. But, for many hunters, their equipment goes far beyond that simple collection. The skilled, experienced hunter will have a variety of materials at hand. These are generally secured in portable containers for protection and ease of access.

An experienced hunter knows the habits of the prey that he is hunting. The time of day that an animal moves about their environment, the type of food that they eat, the sounds they make, and other similar practices and routines are researched and studied by the knowledgeable, prepared hunter. These traits are especially critical when the animal that is being hunted is in the big game category. It is these animals that are generally more cautious and more sensitive to changes in their environment.

Deer hunters typically are very thorough in their preparations for an outing. They may wear camouflage clothing, erect a tree stand, and establish a shooting zone. Each of these steps may require a specific amount of time and effort in order to ensure their appropriateness for the time of year and geographic location.

Scent lures are used to attract large game animals to a particular area. One type of scent lure is deer urine. It is set up in a selected area where the movement of the wind causes the scent to be distributed through the air. On days when the air is calm, the scent fails to be circulated as well as would be desired.

In addition, a hunter may desire to set up his staging area in the early dawn hours while it is still dark. Rather than turn on a bright, flood-type light normally exhibited with an ordinary battery-powered lantern which may pre-warn a prey that an adversary is in the area, preferably the hunter has a light that radiates a light only onto a limited area, such as a spot-type light.

Further, when a hunter is setting up his staging area and to minimize disturbances that might betray his presence to a prey, preferably the hunter will have to make only one trip to the staging site will all of his equipment, including weapons, ammunition, portable tree stand, etc. substantial further additions to his hunting repertoire may make this one-trip in scenario next to impossible.

What is needed is a scent-distributing mechanism combined with a spot-type lantern.

SUMMARY OF THE INVENTION

The improvements of the combination scent-distributor/flashlight of the present invention include a light-producing portion having a first housing with a front end and a rear end, a narrow central portion, a rechargeable battery, an illumination mechanism operably and electrically connected to the rechargeable battery wherein the illumination mechanism is mounted to the front end of the housing, a multi-position switch mechanism structured and configured to control flow of electrical energy from the rechargeable battery to the illumination mechanism, and a first adapting mechanism having a plurality of female connectors wherein each female connector is electrically connected to, and controlled by, the multi-position switch mechanism.

The improvements of the combination scent-distributor/flashlight of the present invention also include a scent-producing portion having a second housing with a cavity, at least one intake vent, and at least one output vent; a second adapting mechanism having a plurality of male connectors structured and configured to mate with the female connectors of the first adapting mechanism to removably and physically connect the scent-producing and light-producing portions together as a unit, and to electrically connect the plurality of male connectors to the multi-position switch mechanism of the light-producing portion; a container containing a scent and having a wick structured and configured to slowly release the scent contained in the container, the container being dimensioned to be slidably insertable into the cavity, and a motor-driven fan mechanism structured and configured to operatively draw ambient air through the at least one intake vent, to circulate that air across and around the wick, and to exhaust that air through the at least one output vent, the motor-driven fan mechanism being connected to, and controlled by electrical connections through the male and female connectors of the first and second adapting mechanisms.

The illumination mechanism may provide a high-intensity flood-type light output and/or a low-intensity spot-type light output controlled by the multi-position switch mechanism.

The combination scent-distributor/flashlight may also have a recharging mechanism that is structured and configured to be plugged into a household electrical receptacle. In that event, the recharging mechanism may be mounted such that a plug thereof may be pivotally mounted such that the connection portion can be displaced outside the first housing for recharging purposes and be displaced inside the first housing when not being used.

The recharging mechanism may also include a recharging adapter having an elongate flexible recharging cord with a female adapter on one end thereof, wherein the female adapter is structured to be plugged into a cigarette lighter of a motor vehicle, and a male adapter on the other end thereof for plugging into a female charging adapter in the first housing. In that event, the first housing may include a compartment for storing the recharging cord when not being used.

The combination scent-distributor/flashlight for a hunter may also include a hook mounted to the rear end of the first housing wherein the hook is structured to be hooked over a low-lying branch of a tree or shrub so light from the light-producing portion can be directed downwardly without being held, or so the combination scent-distributor/flashlight can be suspended from the hunter's belt, for example.

Preferably, the hook is pivotally mounted such that the hook can be displaced outside the first housing when being used, and be displaced inside the first housing when not being used.

The combination scent-distributor/flashlight for a hunter may also include a mounting stud that is mounted to the rear end of the first housing, wherein the mounting stud is structured and configured to removably mount the combination scent-distributor/flashlight to a hunting implement.

PRINCIPAL OBJECTS AND ADVANTAGES OF THE INVENTION

The principal objects and advantages of the present invention include: providing an apparatus that can be used by hunters as a portable scent-distributing device; providing such an apparatus that can also be used as a spot- or flood-type, high intensity and/or low-intensity light; and generally providing such an apparatus that is reliable in performance, capable of long lasting life, and particularly well adapted for the proposed usages thereof.

Other objects and advantages of this invention will become apparent from the following description taken in conjunction with the accompanying drawings wherein are set forth, by way of illustration and example, certain embodiments of this invention.

BRIEF DESCRIPTION OF THE DRAWING FIGURES

FIG. 1 is a perspective view of a light-producing portion of a combination scent-distributor/flashlight for a hunter in accordance with the present invention.

FIG. 2 is perspective view of a scent-producing portion of the combination scent-distributor/flashlight for a hunter.

FIG. 3 is a perspective view of a scent container of the combination scent-distributor/flashlight for a hunter.

FIG. 4 is a perspective view of a recharging cord of the combination scent-distributor/flashlight for a hunter in accordance with the present invention.

DETAILED DESCRIPTION OF THE INVENTION

As required, embodiments of the present invention are disclosed herein, however, it is to be understood that the disclosed embodiments are merely exemplary of the invention, which may be embodied in various forms. Therefore, specific structural and functional details disclosed herein are not to be interpreted as limiting, but merely as a basis for claims and as a representative basis for teaching one skilled in the art to variously employ the present invention in virtually any appropriately detailed structure.

The reference numeral 10 generally refers to a combination scent-distributor/flashlight for a hunter in accordance with the present invention, as shown in FIGS. 1 through 4. It is to be understood that the combination scent-distributor/flashlight 10 of the present invention may be used for various types of animals, including without limitation deer, elk, cougar, etc., depending on the type of scent utilized by the combination scent-distributor/flashlight 10 as described herein.

The combination scent-distributor/flashlight for a deer hunter 10 comprises a light-producing portion 22 and a scent-producing portion 24. The light-producing portion 22 includes a first housing 26 having a front end 28 and a rear end 30, a narrow central portion 31, a rechargeable battery 32, and an illumination mechanism 34 operably and electrically connected to the rechargeable battery 32. The illumination mechanism 34 is mounted to the front end 28 of the first housing 26. The combination scent-distributor/flashlight 10 also includes a multi-position switch mechanism 36 that is structured and configured to control flow of electrical energy from the rechargeable battery 32 to the illumination mechanism 34, and a first adapting mechanism 38 having a plurality of female connectors 40, each female connector 40 electrically connected to, and controlled by, the multi-position switch mechanism 36.

Preferably, the illumination mechanism 34 of the combination scent-distributor/flashlight 10 has a high-intensity light output and a low-intensity light output, each controlled by the multi-position switch mechanism 36. If desired, the low-intensity light output may be either spot-type or flood-type illumination, preferably spot-type, and the high-intensity light output may be either flood-type or spot-type illumination, preferably flood-type.

The scent-producing portion 24 includes a second housing 52 having a cavity 54, at least one intake vent 56, and at least one output vent 58; a second adapting mechanism 60 having a plurality of male connectors 62 structured and configured to mate with the female connectors 40 of the first adapting mechanism 38 to removably and physically connect the scent-producing and light-producing portions 22, 24 together as a unit, and electrically connect the plurality of male connectors 62 to the multi-position switch mechanism 36 of the light-producing portion 22.

The scent-producing portion 24 also includes a container 70 containing a scent 72 and a wick 74 that is structured and configured to slowly release the scent 72 contained in the container 70 wherein the container 70 is dimensioned to be slidably insertable into the cavity 54.

The scent-producing portion 24 also includes a motor-driven fan mechanism 76 that is structured and configured to operatively draw ambient air through the at least one intake vent 56, to circulate that air across and around the wick 74, and to exhaust that air through the at least one output vent 58, the motor-driven fan mechanism 76 being connected to, and controlled by electrical connections through the male and female connectors 62, 40 of the first and second adapting mechanisms 38, 60.

The combination scent-distributor/flashlight 10 may also include a hook 80 mounted to the rear end 30 of the first housing 26 wherein the hook 80 is structured to be hooked over a low-lying branch of a tree or shrub so light from the light-producing portion 22 can be directed downwardly without being held, or so the combination scent-distributor/flashlight 10 can be suspended from the hunter's belt, for example. Preferably, the hook 80 is pivotally mounted such that the hook 80 is displaced outside the first housing 26 when being used, and displaceable to be within the confines of the first housing 26 when not being used, as indicated by the arrow designated by numeral 82 in FIG. 1.

The combination scent-distributor/flashlight 10 may further include a mounting stud 84 that is mounted to the rear end 30 of the first housing 26. The mounting stud 84 is structured and configured to removably mount the combination scent-distributor/flashlight 10 to a hunting implement. Preferably, the stud 84 is pivotally mounted such that the stud 84 is displaced outside the first housing 26 when being used, and displaceable to be within the confines of the first housing 26 when not being used, as indicated by the arrow designated by numeral 85 in FIG. 1.

The combination scent-distributor/flashlight 10 may include a recharging mechanism 86 having a plug 88 that is structured and configured to be connected to a household electrical receptacle (not shown). Preferably, the plug 88 is pivotally mounted such that the plug 88 can be displaced outside the first housing 26 for recharging purposes and displaceable to be within the confines of the first housing 26 when not being used.

In addition, the recharging mechanism 86 may include a female adapter 90 mounted to the first housing 26; an elongate flexible recharging cord 92 having a first end 94, structured to be insertable into a cigarette lighter device of a motor vehicle, and a second end 96 having a jack 98 structured to be insertable into the female adapter 90 mounted to the first housing 26. In that event, the combination scent-distributor/flashlight 10 also generally includes a compartment 99 in the first housing 26 for storing the recharging cord 92 when not being used.

In an application of the combination scent-distributor/flashlight 10 of the present invention, if a hunter is going to a stakeout, the scent-producing portion 24 is physically connected to the light-producing portion 22 for convenience of transportation by inserting the male connectors 62 into the female connectors 40. If the scent-distributor/flashlight 10 is being carried in the hunter's hand, the hunter simply wraps his fingers through the slot formed between the narrow central portion 31 of the first housing 26 and the second housing 52.

If it is dark, the hunter can manipulate the switch mechanism 36 to cause the light-producing mechanism 22 to illuminate his path. If he is in a region where the light would not alarm his potential prey, the hunter may want to use a high intensity flood-type illumination. However, if he is in a region where the light might alarm his potential prey, the hunter may want to use a low intensity spot-type illumination.

After the hunter has set up his stakeout, the hook 80 is displaced to extend outwardly from the first housing 26 and the combination scent-distributor/flashlight 10 is hung from a limb of a tree or shrub and the switch mechanism 36 is manipulated to activate the motor-driven fan mechanism 76 whereupon ambient air is pulled through the intake vents 56, across the wick 74, and out through output vents 58 into the open air therebelow. If there is a breeze, the stakeout is positioned upstream from the anticipated position of potential prey so the breeze will carry the scent distributed by the combination scent-distributor/flashlight 10 in that general direction.

If the combination scent-distributor/flashlight 10 should need to be recharged while in a remote location, the recharging cord 92 may be used to recharge the battery 32 with a cigarette lighter connection of a vehicle. If the combination scent-distributor/flashlight 10 needs to be recharged and is located where a household receptacle is available, plug 88 may be used for that purpose.

It is to be understood that while certain forms of the present invention have been illustrated and described herein, it is not to be limited to the specific forms or arrangement of parts as described and shown.

What is claimed and desired to be covered by Letters Patent is:

1. A combination scent-distributor/flashlight for a hunter, comprising:
    (a) a light-producing portion including:
        (1) a first housing having a front end and a rear end,
        (2) a rechargeable battery,
        (3) an illumination mechanism operably and electrically connected to the rechargeable battery, the illumination mechanism mounted to the front end of the first housing,
        (4) a multi-position switch mechanism structured and configured to control flow of electrical energy from the rechargeable battery to the illumination mechanism, and
        (5) a first adapting mechanism having a plurality of female connectors, each female connector electrically connected to, and controlled by, the multi-position switch mechanism; and
    (b) a scent-producing portion including:
        (1) a second housing having a cavity, at least one intake vent, and at least one output vent,
        (2) a second adapting mechanism having a plurality of male connectors structured and configured to mate with the female connectors of the first adapting mechanism to:
            (A) removably and physically connect the scent-producing and light-producing portions together as a unit, and
            (B) electrically connect the plurality of male connectors to the multi-position switch mechanism of the light-producing portion;
        (3) a container containing a scent and a wick structured and configured to release the scent contained in the container, the container being dimensioned to be slidably insertable into the cavity, and
        (4) a motor-driven fan mechanism structured and configured to operatively draw ambient air through the at least one intake vent, to circulate that air across and around the wick, and to exhaust that air through the at least one output vent, the motor-driven fan mechanism being connected to, and controlled by electrical connections through the male and female connectors of the first and second adapting mechanisms.

2. The combination scent-distributor/flashlight for a hunter as described in claim 1, wherein the illumination mechanism has a high-intensity flood-type light output and a low-intensity spot-type light output, both controlled by the multi-position switch mechanism.

3. The combination scent-distributor/flashlight for a hunter as described in claim 1, further comprising a recharging mechanism structured and configured to be plugged into a household electrical receptacle.

4. The combination scent-distributor/flashlight for a hunter as described in claim 3, wherein the recharging mechanism is pivotally mounted such that a connection portion thereof can be displaced outside the first housing for recharging purposes and displaceable to be within the confines of the first housing when not being used.

5. The combination scent-distributor/flashlight for a hunter as described in claim 3, wherein the recharging includes a recharging mechanism in the first housing structured and configured to recharge the battery, the recharging mechanism including a female adapter mounted to the first housing; an elongate flexible recharging cord having a first end, structured to be insertable into a cigarette lighter device of a motor vehicle, and a second end having a jack structured to be insertable into the female adapter mounted to the first housing.

6. The combination scent-distributor/flashlight for a hunter as described in claim 5, further comprising a compartment in the first housing for storing the recharging cord when not being used.

7. The combination scent-distributor/flashlight for a hunter as described in claim 1, further comprising a hook mounted to the rear end of the first housing.

8. The combination scent-distributor/flashlight for a hunter as described in claim 7, wherein the hook is pivotally mounted such that the hook is displaced outside the first housing when being used and is displaceable to be within the confines of the first housing when not being used.

9. The combination scent-distributor/flashlight for a hunter as described in claim 1, further comprising a mounting stud is mounted to the rear end of the first housing, wherein the mounting stud is structured and configured to removably mount the combination scent-distributor/flashlight to a hunting implement.

* * * * *